United States Patent [19]

Tullsen

[11] Patent Number: 4,700,059

[45] Date of Patent: Oct. 13, 1987

[54] CHROMATOGRAPHIC OPTICAL DETECTOR WITH IOGARITHMIC CALIBRATION CIRCUIT

[75] Inventor: Thomas R. Tullsen, San Jose, Calif.

[73] Assignee: Dionex Corporation, Sunnyvale, Calif.

[21] Appl. No.: 839,105

[22] Filed: Mar. 13, 1986

[51] Int. Cl.[4] ...................... G01D 18/00; G12B 13/00
[52] U.S. Cl. ........................... 250/214 AG; 250/252.1
[58] Field of Search ......... 250/214 AG, 252.1, 214 L; 356/410, 319, 323, 324, 325; 330/129, 279

[56] References Cited

U.S. PATENT DOCUMENTS

| | | | |
|---|---|---|---|
| 4,133,008 | 1/1979 | Tisue | 250/214 AG |
| 4,263,560 | 4/1981 | Ricker | 330/129 |

FOREIGN PATENT DOCUMENTS 2087181  5/1982  United Kingdom ................ 330/129

Primary Examiner—David C. Nelms
Assistant Examiner—Chung Seo
Attorney, Agent, or Firm—Flehr, Hohbach, Test, Albritton & Herbert

[57] ABSTRACT

An optical detector is provided. The optical detector provides automatic zeroing of a logarithmic ration function in applications such as absorption meters, fluorometers and other chromatographic techniques.

4 Claims, 2 Drawing Figures

CHROMATOGRAPHIC OPTICAL DETECTOR WITH IOGARITHMIC CALIBRATION CIRCUIT

BACKGROUND OF THE INVENTION

The present invention relates to a chromatographic optical detector.

Chromatography is a separation process whereby individual chemical compounds which were originally present in a mixture are resolved or distinguished from one another. In some chromatographic applications, an optical detector can be utilized. In order to properly initialize prior art optical detectors utilized in chromatography applications, a logarithmic ratio (log ratio) circuit takes the log ratio of a first reference signal and a second chromatographic signal, which is typically representative of the absorption of a chemical solution. The reference signal is derived by splitting off and detecting a fixed proportion of the light source which serves to correct for changes in light intensity. The output of the log ratio circuit is an output signal representative of the log ratio of the first and second signals. The prior art typically requires some form of DC voltage or current signal which is subtracted from the output of the log ratio circuit to provide an initial zero value. This approach consequently requires a DC voltage or current circuit in conjunction with the log ratio circuit, thereby increasing the cost and complexity of the optical detector. By initially forcing the output voltage to zero, it is implied that the working liquid in the detector has zero absorption.

With the introduction of the material being analyzed, the working liquid becomes more absorbing, and thus the output from the log ratio circuit becomes a measure of sample concentration. Without this automatic zeroing feature, a large constant offset error would exist due to the difficulty of providing a reference signal equal to the initial chromatographic signal by mechanical/optical/chemical means. This constant offset is typically very large compared with the chromatographic signal.

Log ratio circuits typically include a pair of matched transistors having similar current and voltage characteristics. The log ratio transistors must conform accurately to the true voltage/current curves, as any departure results in a further offset error when the temperature varies.

This usually requires that the transistors, even though matched, must be placed within an oven for proper operating conditions, which necessarily further increases the cost of the overall optical detector circuit. Also, temperature variance problems are still encountered with such prior art approaches.

The DC reference voltage or current circuit and oven requirements are characteristics of prior art approaches for chromatographic optical detectors which increase the overall cost and complexity of such detectors.

SUMMARY OF THE INVENTION

It is an object of the present invention to provide an improved optical detector.

It is another object of the present invention to provide an improved chromatographic optical detector.

It is a more particular object to provide a chromatographic optical detector that eliminates the need for prior art ovens and further eliminates the need for prior art DC voltage or current reference circuits.

Briefly, in one preferred embodiment, the present invention includes a gain control circuit for receiving a first signal representative of the absorption of a chromatographic system. The gain control circuit is further responsive to a gain control signal for generating a second signal which is representative of the changed gain of the first signal. The changed gain can either be increased or decreased gain, depending upon initial operating conditions.

The chromatographic optical detector further includes a logarithmic ratio circuit responsive to a first adjustable signal of the chromatographic system, and responsive to the second reference signal for producing a log ratio output signal of zero. The advantage of initializing the detector with equal inputs to the log ratio circuit is that even though the log ratio transistors do not conform perfectly to the ideal log characteristics (since they are operating at nearly the same current), the output of the transistors will match with temperature variations and hence cancel. Thus, the detector output will not drift away from the initial zero output until the presence of the substance being detected causes a change of amplitude in the chromatographic signal. The optical detector also includes a logic circuit responsive to the log ratio output signal for generating the gain control signal to provide the necessary adjustment or change in the gain of the first signal to enable the adjustment of the output signal to a zero value.

Other objects, advantages and features of the present invention will become apparent from the following detailed description when taken in conjunction with the accompanying drawings.

DETAILED DESCRIPTION OF THE DRAWINGS

Figure 1:
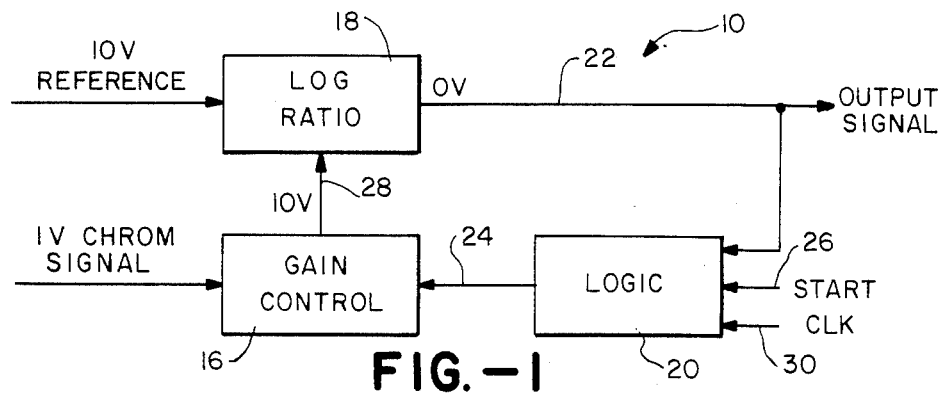
FIG. 1 depicts a block diagram of a chromatographic optical detector according to the present invention.

Referring now to FIG. 1, a block diagram of a chromatographic optical detector 10 according to the present invention is depicted.

An optical detector used with chromatographic systems desirably provides an initial zero value output signal based upon the logarithmic ratio of a first signal representing the absorption of the chromatographic system when compared with a second reference signal of some kind. In a preferred embodiment, the present invention is intended to be used as an optical detector for chromatographic systems. However, the aspects of the present invention can be utilized with other types of optical detection techniques.

As also previously described, prior art optical detector systems take the logarithmic ratio of first and second signals and provide a zero value output by some form of voltage or current injected after the log circuit. In addition, the prior art approaches require matched transistors encapsulated or contained within a suitable oven, which increases the cost of the overall detector.

In FIG. 1, the present invention eliminates the need of such an oven type circuit and provides for improved zeroing of the reference and chromatographic signals in the following manner.

The chromatographic signal on lead 12 is input to gain control circuit 16, which provides an output on lead 28 which typically is an increased or decreased gain control signal corresponding to the chromatographic signal on lead 12. As an example, if the value of the chromatographic signal on lead 12 is one volt, and the value of the reference signal on lead 14 is ten volts, gain control circuit 16 increases the value of the signal on lead 12 to ten volts (as indicated on lead 28).

Log ratio circuit 18 receives the reference signal on lead 14 and the gain control signal on lead 28 to provide a zero value output signal on output lead 22.

In FIG. 1, logic circuit 20 receives the output signal on lead 22 and provides a logic control signal on lead 24 for controlling gain control circuit 16. In a preferred embodiment, logic circuit 20 receives digital control signals identified as Start signal 26 and Clock signal 30. The Start and Clock signals can easily be generated and need not be described in any great detail. The feedback arrangement of logic circuit 20 thus provides necessary control for gain control circuit 16 to either increase or decrease the value of the chromatographic signal on lead 12, as necessary.

For the example indicated in FIG. 1, gain control circuit 16 increases the chromatographic signal on lead 12 to a value of ten volts on lead 28. Log ratio circuit thus will provide the logarithmic ratio of the reference signal (ten volts) on lead 14 and the gain control signal on lead 28 (also ten volts) to provide a zero value signal on lead 22, which is the desired and necessary signal for initial operating conditions (the log of 10/10=0).

If the chromatographic signal on lead 12 were to have a different value, the gain control circuit 16 and logic circuit 20 provide the necessary adjustment to the gain control signal on lead 28, so that log ratio circuit could provide the necessary and desired zero value signal on lead 22.

It can be seen with the feedback arrangement, according to the present invention depicted in FIG. 1, that a DC reference voltage or current circuit is not necessary, as with prior art approaches. As will be described in more detail in conjunction with the circuitry depicted in FIG. 2, the ovens for the matched transistors of a log ratio circuit are also no longer necessary, thereby obviating the increased cost requirements of prior art approaches.

Figure 2:
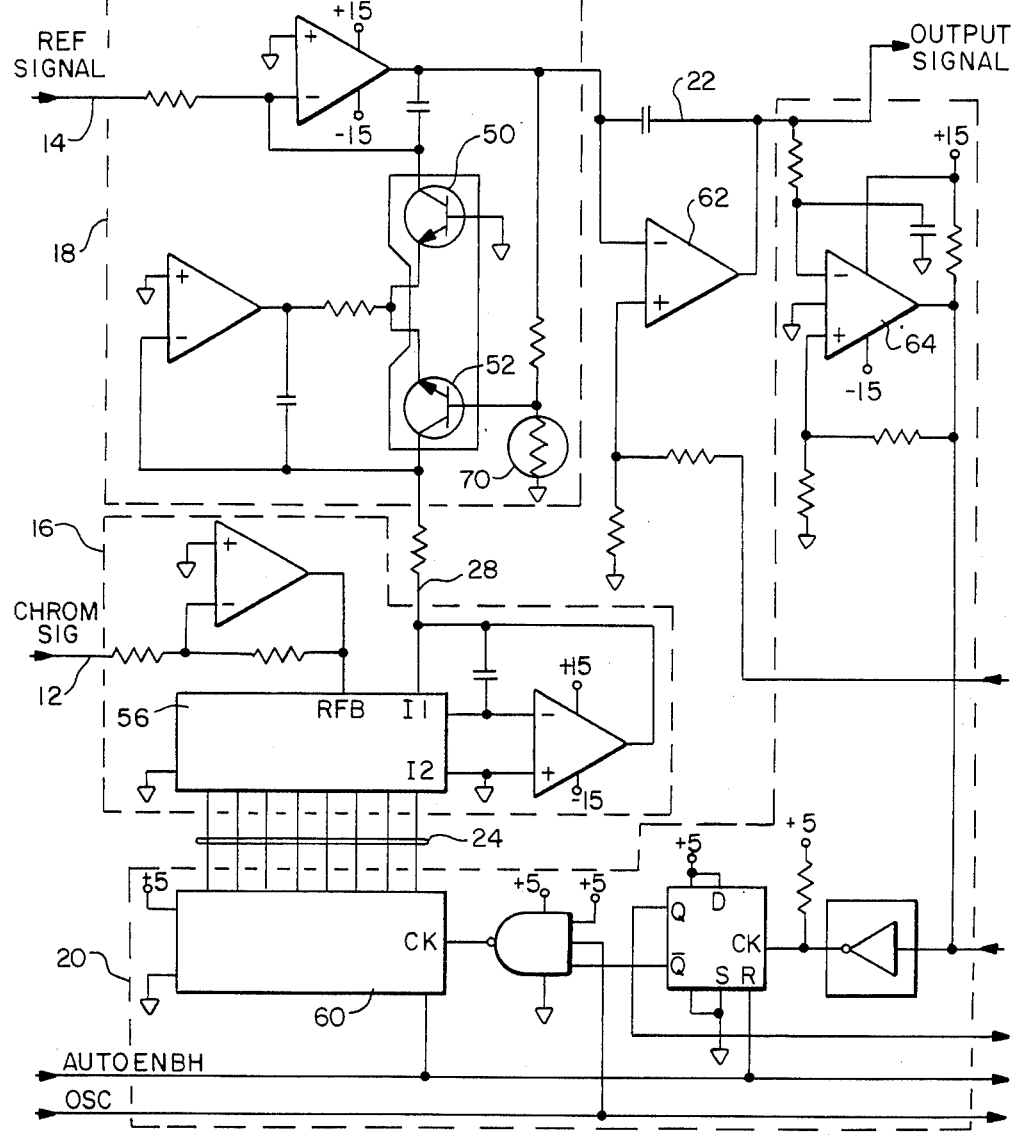
FIG. 2 depicts a schematic diagram of the improved chromatographic optical detector of FIG. 1.

Referring now to FIG. 2, a schematic diagram of the chromatographic optical detector 10 of FIG. 1 is depicted.

In FIG. 2, the log ratio circuit 18 includes a pair of matched transistors 50, 52 which could be typically model numbers LM394. The reference signal on lead 14 is input to log ratio circuit 18 and the chromatographic signal on lead 12 is input to gain control circuit 16.

In FIG. 2, gain control circuit 16 desirably includes a digital-to-analog converter (DAC) 56, which receives a digital control signal from logic circuit 20 via lead 24.

In desirable operation, the control signal on lead 24 of FIG. 1 is generated by "counting" between values of zero and 255 to provide suitable changes in the gain of the chromatographic signal on lead 12. In operation, gain control circuit 16 receives a digital code from a counter 60 which can range in values from, in a preferred embodiment, between digital zero and digital 255. This output signal on lead 24 of FIG. 2 thus enables gain control circuit to automatically change or adjust the chromatographic signal on lead 12 to form the second signal on lead 28.

In FIG. 2, the output of gain control circuit 16 is input to log ratio circuit 18 (together with the reference signal on lead 14) and the output of log ratio circuit 18 is input to a suitable amplifier 62, which is provided for sensitivity purposes and need not be further described in detail.

In FIG. 2, logic circuit 20 includes a comparator 64 for comparing the value of the output signal on lead 22 to determine the necessary loading of counter circuit 60 with an appropriate "code," the value of which can range from digital 0–255. This provides a range of 256 different values for connection to digital-to-analog circuit 56 of the gain control circuit 16.

As an example, if the value of the output from log ratio circuit 18 increases, logic circuit 20 via comparator 64 will provide an indication through the internal logic to counter 60 to appropriately adjust the output of gain control circuit 16 via lead 28.

Consequently, it can be seen that the optical detector of FIG. 2 provides for suitable feedback adjustment of the output signal of the log ratio circuit 18 to a zero value, as appropriate.

Log ratio circuit 18 of FIG. 2 desirably includes matched tranistors 50, 52. The present invention provides for temperature variance compensation under desired operating conditions without the prior art requirements of ovens.

quirements of ovens. In FIG. 2, the thermistor 70 provides improved calibration accuracy, inasmuch as there is a temperature dependent gain factor within the log ratio circuit 18. It has been observed that thermistor 70 provides an order of magnitude improvement.

In a desired embodiment, the gain control circuit of FIGS. 1 and 2 includes a digital counter driving a CMOS digital-to-analog converter.

With the temperature variance not a factor, it is expected that the present invention will work in environments even if the input signals are at variance (if, for example, the light intensity changes for some reason).

Further, the operating range can be effectively extended with the use of a log ratio circuit in conjunction with a gain control circuit, as depicted in FIGS. 1 and 2. The gain of a low input signal is boosted which, with logarithmic applications, provides a better operating range.

The principles of the present invention can be applied to other optical detector applications, such as absorption meters, fluorometers, and the like. Therefore, it is intended that the scope of the present invention be limited only by the accompanying claims.

What is claimed is:

1. An optical detector comprising gain control means for receiving a first signal representative of a first value, said gain control means responsive to a gain control signal for generating a second signal to control the changing of the value of said first signal, log ratio means responsive to a reference signal and to said second signal for generating an output signal adjustable to a zero value, and logic means responsive to said output signal for generating said gain control signal such that said output signal is adjusted a zero value.

2. A chromatographic optical detector comprising gain control means for receiving a first signal representative of the absorption of a chemical solution, said gain control means responsive to a gain control signal for generating a second signal to change the value of said first signal, log ratio means responsive to a reference signal and to said second signal for generating an output signal adjustable to a zero value, and logic means responsive to said output signal for generating said gain control signal to thereby provide for changing said output signal to a zero value.

3. A detector as in claim 2 wherein said logic means include a comparator means for determining the value of said output signal.

4. A detector as in claim 3 wherein said logic means include a digital counter responsive to said comparator means for counting between predetermined values to generate said gain control signal and wherein said gain control means include digital-to-analog converter means responsive to said gain control signal for changing the value of said first signal.

* * * * *